(12) United States Patent
Fujii et al.

(10) Patent No.: US 7,074,374 B1
(45) Date of Patent: Jul. 11, 2006

(54) STERILIZING AGENT CAPSULE CONTAINER AND STERILIZER

(75) Inventors: Keiji Fujii, Yamanashi (JP); Ken Orii, Yamanashi (JP); Katsumi Takahashi, Tokyo (JP)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/936,151

(22) PCT Filed: Mar. 17, 2000

(86) PCT No.: PCT/JP00/01681

§ 371 (c)(1),
(2), (4) Date: Apr. 15, 2002

(87) PCT Pub. No.: WO00/55070

PCT Pub. Date: Sep. 21, 2000

(30) Foreign Application Priority Data

Mar. 17, 1999 (JP) .................... 11/72506
Mar. 17, 1999 (JP) .................... 11/72507

(51) Int. Cl.
*A61L 2/00* (2006.01)
(52) U.S. Cl. .................. 422/292; 206/538; 222/83; 222/85; 422/294; 422/297; 422/300
(58) Field of Classification Search ........... 422/292, 422/294, 297, 300; 206/538; 222/83, 85
See application file for complete search history.

(56) References Cited

U.S. PATENT DOCUMENTS

| 821,519 | A | 5/1906 | Mitchell |
| 1,636,983 | A | 7/1927 | Broadmeyer |
| 1,767,914 | A | 6/1930 | Boudin |
| 2,780,982 | A | 2/1957 | Malone et al. |
| 4,590,037 | A | * | 5/1986 | Kaye .................... 422/116 |
| 4,643,867 | A | 2/1987 | Hornak et al. |
| 4,817,800 | A | 4/1989 | Williams et al. |

(Continued)

FOREIGN PATENT DOCUMENTS

CH 676 284 A 12/1990

(Continued)

OTHER PUBLICATIONS

U.S. Appl. No. 09/864,470, filed May 24, 2001.

(Continued)

*Primary Examiner*—Krisanne Jastrzab

(57) ABSTRACT

In a sterilizing agent capsule container and a sterilizer using the sterilizing agent capsule container where a vacuum sterilizing housing is filled with a chemical vapor obtained by the vaporization of a sterilizing agent to sterilize an object to be sterilized, a plurality of sealed sterilizing agent capsules are accommodated in the axial direction of a needle for removing a sterilizing agent in a capsule accommodation chamber of the sterilizing agent capsule container and the sealed sterilizing agent capsules are made of a material through which the needle can pass. A plurality of the sealed sterilizing agent capsules in the sterilizing agent capsule container can be gradually punctured by the needle in sequence. Thus, a moving device for horizontally moving the sterilizing agent capsule container and displacing sealed sterilizing agent capsules to a removal position corresponding to the needle, and a pressurizing device for compressing and pressuring the sealed sterilizing agent capsules at the removal position are not particularly required. As a result, the space occupied by the sterilizing agent capsule container can be reduced and the structure thereof can be simplified with a decrease in cost.

13 Claims, 11 Drawing Sheets

U.S. PATENT DOCUMENTS

| | | | |
|---|---|---|---|
| 4,869,286 A | 9/1989 | Williams et al. | |
| D306,065 S | 2/1990 | Williams et al. | |
| D306,066 S | 2/1990 | Williams et al. | |
| 4,899,519 A | 2/1990 | Williams et al. | |
| 4,909,287 A | 3/1990 | Williams et al. | |
| 4,913,196 A | 4/1990 | Williams et al. | |
| D307,794 S | 5/1990 | Williams et al. | |
| 4,938,262 A | 7/1990 | Williams et al. | |
| 4,941,518 A | 7/1990 | Williams et al. | |
| 5,209,909 A * | 5/1993 | Siegel et al. | 422/292 |
| 5,662,866 A * | 9/1997 | Siegel et al. | 422/29 |
| 5,770,739 A | 6/1998 | Lin et al. | |
| 5,858,305 A * | 1/1999 | Malchesky | 422/28 |
| 5,887,716 A | 3/1999 | Williams et al. | |
| 6,279,622 B1 | 8/2001 | Nguyen et al. | |
| 6,412,340 B1 | 7/2002 | Nguyen et al. | |

FOREIGN PATENT DOCUMENTS

| | | |
|---|---|---|
| DE | 22 06 910 A | 8/1973 |
| EP | 0207417 B1 | 1/1987 |
| EP | 0291987 B1 | 11/1988 |
| EP | 0302420 B1 | 2/1989 |
| EP | 0679407 A2 | 11/1995 |
| WO | WO 94 20150 A | 9/1994 |

OTHER PUBLICATIONS

U.S. Appl. No. 10/042,906, filed Jan. 9, 2002.

U.S. Appl. No. 10/042,904, filed Jan. 9, 2002.

Supplementary European Search Report EP 00909741 dated Jan. 28, 2003.

Brieseck H. et al; "Gas Cartridge Puncturing Equipment—Has Thrust Plate With Driving Member Actuated by Hydraulic RAM"; German Patent CH 676 284 A, Dec. 28, 1990; English Abstract Dialog File No. 351 Accession No. 7564936; Derwent World Patents Index; 2003 Derwent Information Ltd.

Munchener Medizin Mechanik; "Sterilisation Chamber Safety Device—with door lock triggered by actuation of gas cartridge piercer"; German Patent DE 2206910A, Aug. 23, 1973; English Abstract Dialog File No. 351 Accession No. 973437; Derwent World Patents Index; 2003 Derwent Information Ltd.

* cited by examiner

STERILIZING AGENT CAPSULE CONTAINER AND STERILIZER

TECHNICAL FIELD OF THE INVENTION

The invention relates to a sterilizing agent capsule container, particularly a sterilizing agent capsule container suitable for use in a low-temperature plasma sterilizer and a sterilizer using the sterilizing agent capsule container.

BACKGROUND OF THE INVENTION

In a conventional low-temperature plasma sterilizer, sealed capsules containing an aqueous hydrogen peroxide solution (hereinafter referred to as a hydrogen peroxide solution) are accommodated in a capsule container for filling a sterilizing chamber with a hydrogen peroxide gas.

A plurality of hydrogen peroxide capsules are horizontallydi sposed and selected in sequence at a certain position for removing a hydrogen peroxide solution. At this time, in order to facilitate the removal of the hydrogen peroxide solution from the capsules, the capsules are pressurized with air compressed by a pressurizing means.

Related techniques include a low pressure hydrogen peroxide vapor sterilizing method disclosed in U.S. Pat. No. 2,780,982, a hydrogen peroxide plasma sterilizing system disclosed in Patent Kokoku S2(1990)-62261 (Patent No. 1636983), a liquid introducing system disclosed in Patent Kokoku H4(1992)-55706 (Patent No. 1767914) and a sterilizing agent distribution cassette for a sterilizer disclosed in Design Registration No. 821519.

In a conventional capsule container, since the hydrogen peroxide capsules are horizontally disposed, they occupy a large space. In addition, since the capsule container requires a removal device provided with a selection mechanism for selecting a hydrogen peroxide capsule, and an exclusive pressurizing means for pressurizing a hydrogen peroxide capsule with compressed air to facilitate the removal of a hydrogen peroxide solution from the capsule, its structure is complicated, thus increasing the cost.

Thus, an object of the invention is to provide a sterilizing agent capsule container and a sterilizer which occupy only a small space and are simple in structure, and where a hydrogen peroxide solution can be securely taken out of capsules.

SUMMARY OF THE INVENTION

According to an aspect of the present invention, there is provided a sterilizing agent capsule container in communication with a reduced-pressure housing of a sterilizer, which comprising: a capsule accommodation chamber, and a plurality of sealed sterilizing agent capsules accommodated in the capsule accommodation chamber in an axial direction of a needle for removing a sterilizing agent, the sealed sterilizing agent capsules made of a material which the needle can pass through.

In the sterilizing agent capsule container thus constructed, a plurality of sealed sterilizing agent capsules can be accommodated in the capsule accommodation chamber in the axial direction of the needle. Consequently, a space occupied by the sterilizing agent capsule container in a sterilizer can be reduced, compared with a conventional capsule container where a plurality of sealed sterilizing agent capsules are packed in a plate state. In addition, since the sealed sterilizing agent capsules are not required to be moved to a position corresponding to a needle in sequence, a moving device therefor is unnecessary, thereby allowing the simplification of the structure and a decrease in cost.

According to another aspect of the present invention, a plurality of capsules is accommodated in the capsule accommodation chamber and at least two of the capsules are sealed sterilizing agent capsules.

In the sterilizing agent capsule container thus constructed, in addition to simplifying the structure and decreasing the cost, the at least two sealed sterilizing agent capsules in the capsule container can be punctured in sequence by the needle without moving the sterilizing agent capsule container for efficient removal of a sterilizing agent.

According to another aspect of the present invention, a plurality of sealed sterilizing agent capsules and a plurality of sealed gas capsules are alternately accommodated in the capsule accommodation chamber.

In such a sterilizing agent capsule container, the sealed sterilizing agent capsules can be stably held by the sealed gas capsules in the capsule accommodation chamber with a cushion effect, and the needle can gradually and smoothly puncture sealed sterilizing agent capsules in sequence.

According to another aspect of the present invention, a plurality of sealed sterilizing agent capsules and a movable capsule support which the needle can pass through are combined and accommodated in the capsule accommodation chamber.

In such a sterilizing agent capsule container, the sealed sterilizing agent capsules can be stably held by the capsule support in the capsule accommodation chamber, and the needle can gradually and smoothly puncture sealed sterilizing agent capsules in sequence.

According to another aspect of the present invention, a plurality of sealed sterilizing agent capsules and a plurality of movable capsule supports are alternately accommodated in the capsule accommodation chamber.

In such a sterilizing agent capsule container, the sealed sterilizing agent capsules can be stably held apart from each other by a certain distance by the capsule supports in the capsule accommodation chamber, and the needle can gradually and smoothly puncture the sealed sterilizing agent capsules in sequence.

According to another aspect of the present invention, a plurality of sealed sterilizing agent capsules, a sealed gas capsule and a movable capsule support which the needle can pass through are combined and accommodated in the capsule accommodation chamber.

In such a sterilizing agent capsule container, the sealed sterilizing agent capsules can be more stably held by the sealed gas capsule and the capsule support in the capsule accommodation chamber with a cushion effect caused by the sealed gas capsule at the holding position, and the needle can gradually and smoothly puncture the sealed sterilizing agent capsules in sequence.

According to another aspect of the present invention, the sealed sterilizing agent capsules and sealed gas capsules or capsule supports are alternately disposed in the capsule accommodation chamber and a sealed sterilizing agent capsule closest to an insert opening of the capsule accommodation chamber is supported by a capsule support movably disposed in the capsule accommodation chamber.

In such a sterilizing agent capsule container, the sealed sterilizing agent capsules can be stably held by the sealed gas capsules or the capsule supports in the capsule accommodation chamber, and since the sealed sterilizing agent capsule closest to an insert opening of the capsule accommodation chamber is supported by the capsule support, the dislocation of a sealed sterilizing agent capsule from the capsule accommodation chamber can be prevented. In addition, since the capsule supports are movable in the capsule accommodation chamber, they do not obstruct the gradual punctures of the sealed sterilizing agent capsules by the needle.

According to another aspect of the present invention, the sterilizing agent in the sealed sterilizing agent capsules is a hydrogen peroxide solution or a peracetic acid solution.

In such a sterilizing agent capsule container, upon puncturing a sealed sterilizing agent capsule, a chemical sterilizing water can be promptly transpired.

According to another aspect of the present invention, the sealed sterilizing agent capsules contain a gas layer therein.

In such a sterilizing agent capsule container, breakage of a sealed sterilizing agent capsule can be prevented to enhance the safety.

According to another aspect of the present invention, there is provided a sterilizer comprising: a sterilizing agent capsule container in communication with a reduced-pressure housing functioning as a sterilization chamber; a plurality of sealed sterilizing agent capsules with a sterilizing agent sealed therein to be mounted in a capsule accommodation chamber of the sterilizing agent capsule container; a needle capable of passing through the sealed sterilizing agent capsules to take the sterilizing agent therefrom; and a driving member for driving the needle or the sterilizing agent capsule container so that the needle can puncture the sealed sterilizing agent capsules in the sterilizing agent capsule container in an axial direction of the needle in sequence.

In such a sterilizer, when the sterilizing agent capsule container with the sealed sterilizing agent capsules accommodated therein or the needle is driven, the sealed sterilizing agent capsules can be punctured by the needle in the capsule accommodation chamber of the sterilizing agent capsule container. Thus, an exclusive moving device for moving a sealed sterilizing agent capsule to a certain removal position, and a large pressurizing device for pressurizing and compressing the sealed sterilizing agent capsule at the removal position are not required. As a result, the construction of the sterilizer can be simplified with decreases in space and cost.

According to another aspect of the present invention, the needle has a pressing part for pressing a sealed sterilizing agent capsule in a direction of compression.

In such a sterilizer, when the needle punctures a sealed sterilizing agent capsule, the sealed sterilizing agent capsule is securely compressed with the pressing part of the needle so that a sterilizing agent can be efficiently and securely taken out of the sealed sterilizing agent capsule.

According to another aspect of the present invention, the sterilizing agent capsule container communicates with the reduced-pressure housing through a diffuser and when the needle punctures a sealed sterilizing agent capsule, the diffuser introduces a sterilizing agent transpired from the sealed sterilizing agent capsule.

In such a sterilizer, the diffuser can prevents a transpired sterilizing agent at the time of puncture from condensing before it reaches the reduced-pressure housing.

According to another aspect of the present invention, a low-temperature plasma is generated in the reduced-pressure housing.

In such a sterilizer, an object to be sterilized can be efficiently sterilized by the low-temperature plasma.

BEST MODE OF CARRYING OUT THE INVENTION

The best mode of carrying out the invention will be described with reference to the attached drawings to illustrate the invention in more detail.

Embodiment 1

Figure 1:
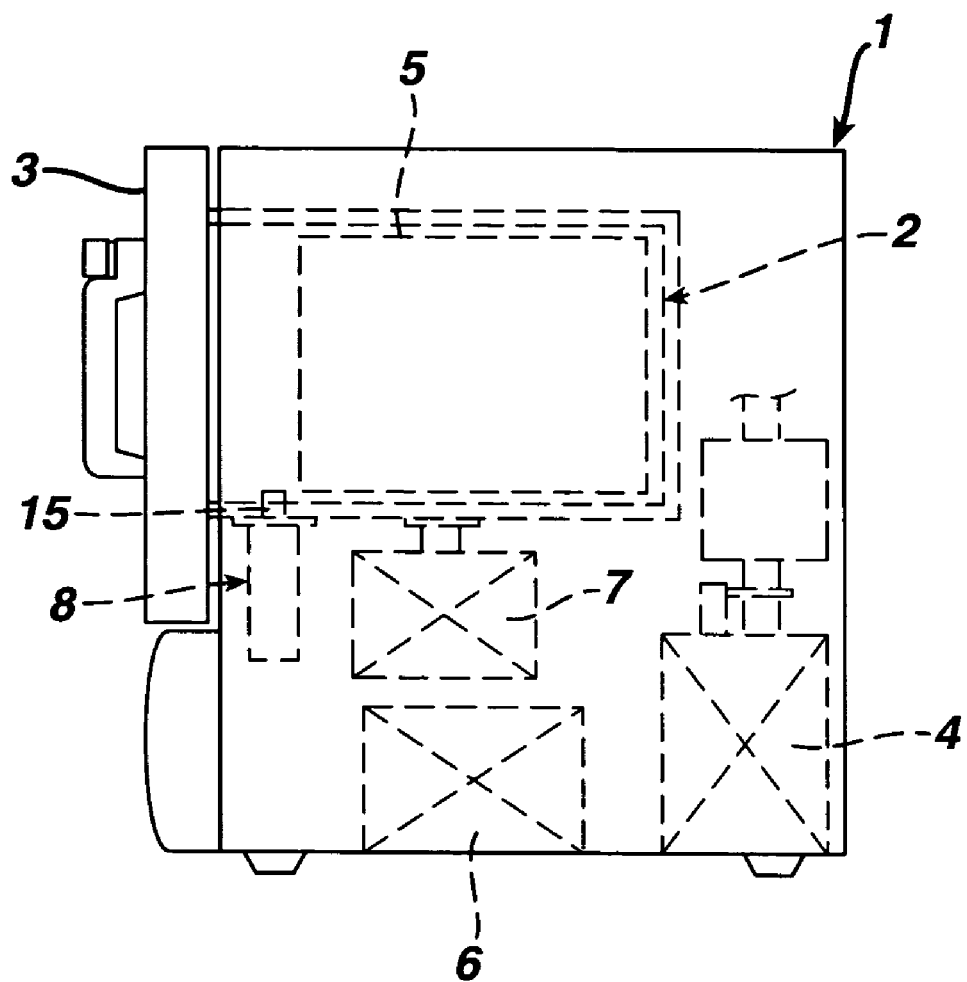
FIG. 1 is a side view showing a sterilizer according to the embodiment 1 of the present invention.

FIG. 1 is a side view showing a low-temperature plasma sterilizer according to the embodiment 1 of the present invention.

In FIG. 1, the reference numeral 2 denotes a vacuum housing (reduced-pressure housing) serving as a sterilizing chamber of a low-temperature plasma sterilizer 1. An object to be sterilized can be placed into or removed from the reduced-pressure housing 2 by opening a front door 3.

The reduced-pressure housing 2 is maintained at a certain vacuum degree with a vacuum pump 4. Although the certain vacuum degree may be any reduced-pressure degree under which the housing 2 can function as a reduced-pressure housing, it is preferably about 0.4 Torr (about 30 Pa). An electrode 5 for generating plasma is disposed about the inner periphery of the reduced-pressure housing 2 and a hydrogen peroxide introducing device 8 for creating a hydrogen peroxide gas atmosphere inside the reduced-pressure housing 2 is disposed on the floor of the housing 2.

The electrode 5 is of a cylindrical shape with the front and rear open ends. A shelf (not shown) where an object to be sterilized is set can be placed in the electrode 5. A RF oscillator 6 transmits a high frequency to the electrode 5, thereby generating plasma. A matching controller 7 controls the resistance value to be constant, thereby obtaining stable plasma.

As shown in FIG. 1, the hydrogen peroxide introducing device 8 has a sterilizing agent capsule container (capsule container) 15, a sterilizing agent removal needle (hereinafter referred to as a needle) 17 for taking a hydrogen peroxide solution out of the sterilizing agent capsule container 15, and a diffuser (evaporator) 19 for preventing the condensation of a mist-like hydrogen peroxide gas (chemical sterilizing agent) taken out by the needle 17.

Figure 2:
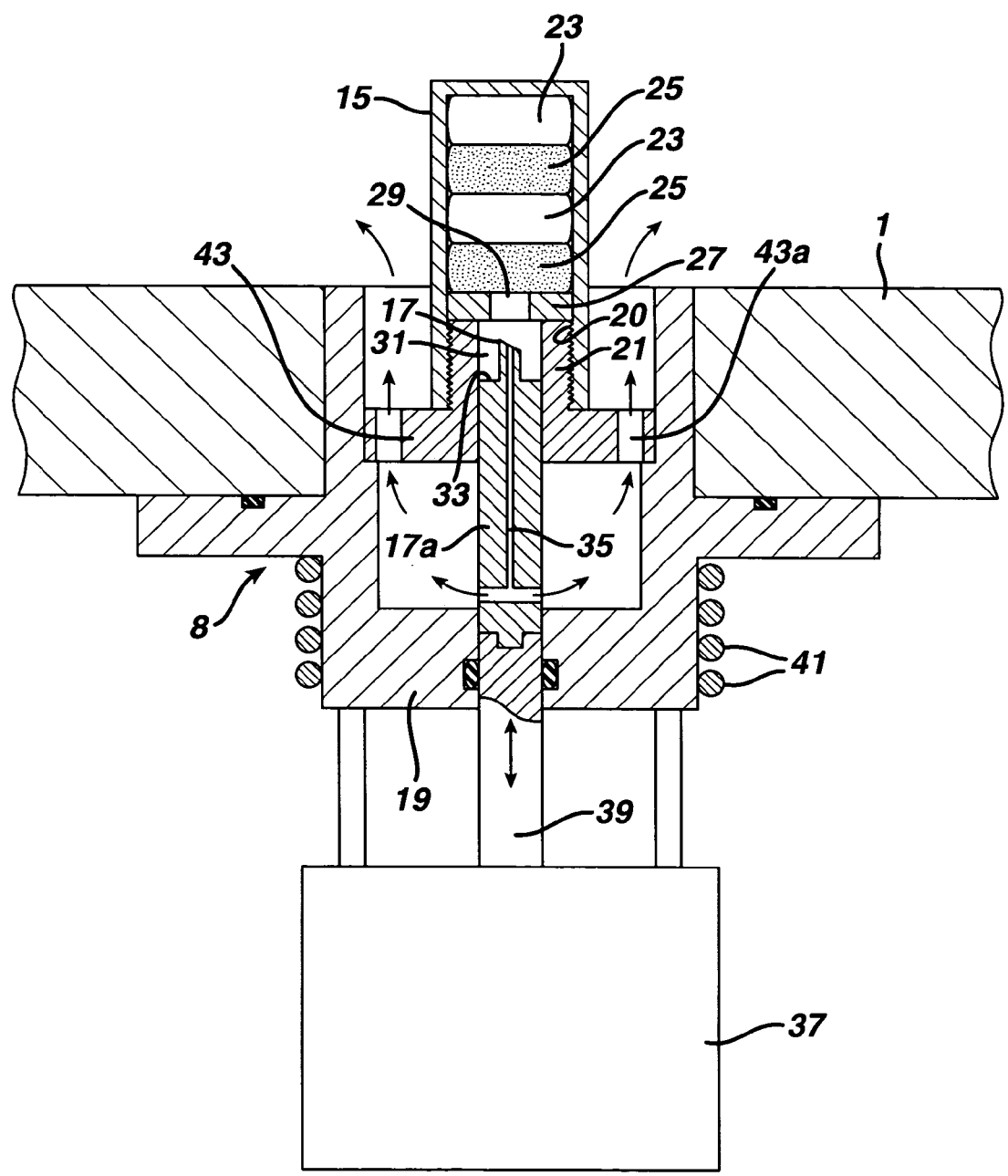
FIG. 2 is an enlarged sectional view of a sterilizing agent introducing device mounted in the sterilizer of FIG. 1.
Figure 3:
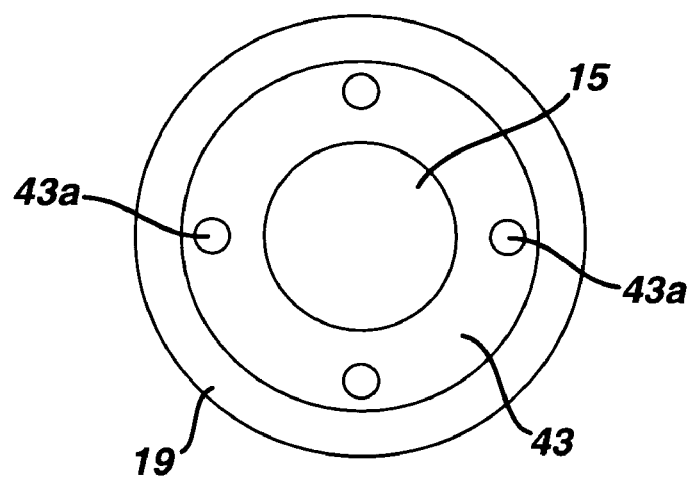
FIG. 3 is a plan view of a part of the sterilizing agent introducing device of FIG. 2 where a sterilizing agent capsule container is mounted.

FIG. 2 is an enlarged sectional view of the hydrogen peroxide introducing device 8 of the low-temperature plasma sterilizer 1. In the figure, the reference numeral 15 denotes a sterilizing agent capsule container of the low-temperature plasma sterilizer 1.

The sterilizing agent capsule container 15 is of a cylindrical shape with an insert open end 20 at the under part of a container body (capsule accommodation chamber) 15A. A female screw part is provided on the inner wall of the open end 20. The female screw part engages a mounting screw part 21 of a diffuser 19 provided in the reduced-pressure housing 2.

Hydrogen peroxide capsules 25 and air capsules 23 inserted from the open end 20 are alternately stacked in the container body 15A. The hydrogen peroxide capsules 25 (hereinafter referred to as a sealed sterilizing agent capsule) contain a hydrogen peroxide solution (hereinafter referred to as a sterilizing agent) and are sealed, while the air capsules 23 (hereinafter referred to as a sealed gas capsule) contain air (gas) and are sealed. The lowest sealed sterilizing agent capsule 25 is supported by a capsule support 27.

The number of the sealed sterilizing agent capsules 25 and sealed gas capsules 23 can be properly selected.

In the embodiment 1, a gas sealed in the sealed gas capsules 23 is air, while a sterilizing agent sealed in the sealed sterilizing agent capsules 25 is a hydrogen peroxide solution.

The sealed sterilizing agent capsules 25 and sealed gas capsules 23 are of a pouch-like shape. They are made of any material which the needle 17 can pass through, for example flexible plastics and gums.

Figure 4:
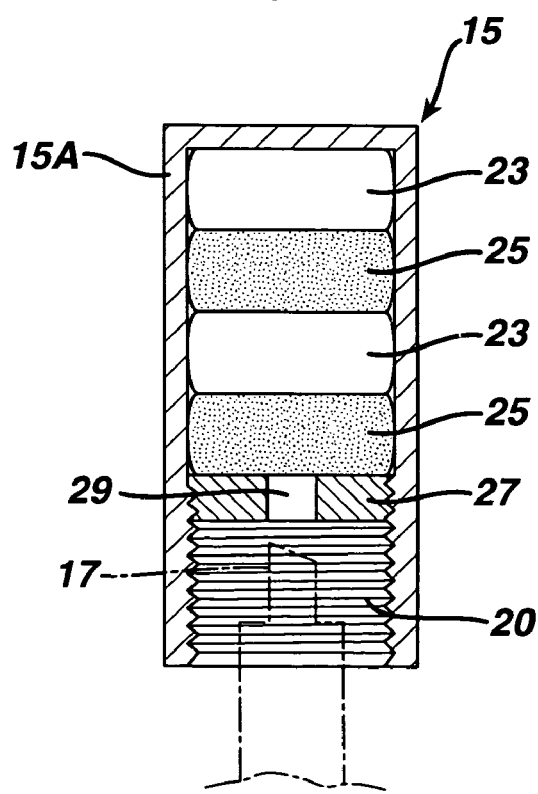
FIG. 4 is an enlarged sectional view of the sterilizing agent capsule container.

The capsule support 27 has an insert hole 29 in the center and a screw part in the periphery. The needle 17 can pass through the insert hole 29. The screw part can be inserted from the open end 20. Once the screw part of the capsule support 27 exceeds the female screw region of the open end 20, as shown in FIG. 4, the male screw disengages with the female screw and can freely move upwardly, while the female screw prevents the support 27 from dropping downwardly.

The capsule container 15 thus constructed can be used as a removable sterilizing agent capsule container 15. The body axis 17a of the needle 17 passes through the diffuser 19, and then slidably enters into a through hole 22 of the mounting screw part 21. The body axis 17a is provided with a pressing part 33 which acts on the bottom surface of the support 27 and raises it upwardly.

The body axis 17a of the needle 17 is supported by a rod 39 of a diving member 37 connected thereto. The rod 39 can move vertically.

The diving member 37 is controlled to lift the needle 17 in two steps corresponding to the locations of the two sealed sterilizing agent capsules 25 stacked vertically. In the first step, it lifts the needle 17 to a position where the needle punctures the under part of the lowest sealed sterilizing agent capsule 25. At this time, the pressing part 33 is placed just short of the bottom surface of the capsule support 27.

In the second step, the diving member 37 further lifts the needle 17. The needle 17 passes through the deflated lowest sealed sterilizing agent capsule 25 and sealed gas capsule 23 to a position where it punctures the under part of the next sealed sterilizing agent capsule 25. The pressing part 33 is lifted together with the needle 17 to raise the deflated capsules.

The diffuser 19 has a heater 41 around its periphery to provide a diffusion function for preventing the condensation of a hydrogen peroxide gas (sterilizing agent) in the form of a mist taken out by the needle 17.

The mist-like hydrogen peroxide diffused by the diffuser 19 is transmitted from a communication port 31 to a reduced-pressure housing 2 or sterilizing chamber. The inside of the reduced-pressure housing 2 is maintained to a specified reduced-pressure by a vacuum pump 4 as shown in FIG. 1.

A sealed gas capsule 23, a sealed sterilizing agent capsule 25, a sealed gas capsule 23 and a sealed sterilizing agent capsule 25 are inserted from the open end 20 into the container body 15A in sequence, and a capsule support 27 is then inserted to support the lowest sealed sterilizing agent capsule 25. The sterilizing agent capsule container 15 is thus prepared wherein the sealed sterilizing agent capsules 25 are vertically separated by air layers (gas layers) of the sealed gas capsules 23.

Next, the open end 20 of the container body 15A is engaged with the mounting screw part 21 of the diffuser 19. Since the sealed sterilizing agent capsules 25 and sealed gas capsules 23 are vertically stacked in the container body 15A, they do not require a large location space in the reduced-pressure housing 2. The remainder of the housing 2 is of a capacity enabling any other use.

Next, the needle 17 is lifted by a given distance to puncture the lowest sealed sterilizing agent capsule 25. At the same time, each sealed gas capsule 23 expands corresponding to the reduced-pressure degree of the reduced-pressure housing 2 to pressurize the lowest sealed sterilizing agent capsule 25. Although the uppermost sealed gas capsule 23 expands to pressurize the adjacent sealed sterilizing agent capsule 25, this is no problem since the needle 17 does not reach this sealed sterilizing agent capsule 25. Thereafter, in the sequence steps, a hydrogen peroxide solution is forced by a pressure applied on a sealed sterilizing agent capsule 25 to pass through the needle 17 to the diffuser 19.

As the amount of the removed hydrogen peroxide solution increases, the sealed sterilizing agent capsule 25 is gradually deflated. The sealed gas capsule 23 increasingly expands corresponding to the deflation to continue pressurizing. Thus, a hydrogen peroxide solution in a sealed sterilizing agent capsule 25 can be securely taken out without any specific pressurizing means.

When the remainder of the hydrogen peroxide solution is reduced, the needle 17 passes through the deflated sealed sterilizing agent capsule 25 and then punctures the upper sealed gas capsule 23. At this time, an air pressure transmits the remaining hydrogen peroxide solution with the air of the sealed gas capsule 23 to the diffuser 19. The sealed gas capsule 23 is simultaneously deflated, but this is no problem since the needle 17 does not reach the next waiting sealed sterilizing agent capsule 25.

Thereafter, the needle 17 is lifted again and punctures the next sealed sterilizing agent capsule 25 to remove a hydrogen peroxide solution. The capsule container 15 used is replaced with a new sterilizing agent capsule container 15 with sealed sterilizing agent capsules 25 and sealed gas capsules 23 therein so that a sterilization operation can be repeated.

Embodiment 2

Figure 5:
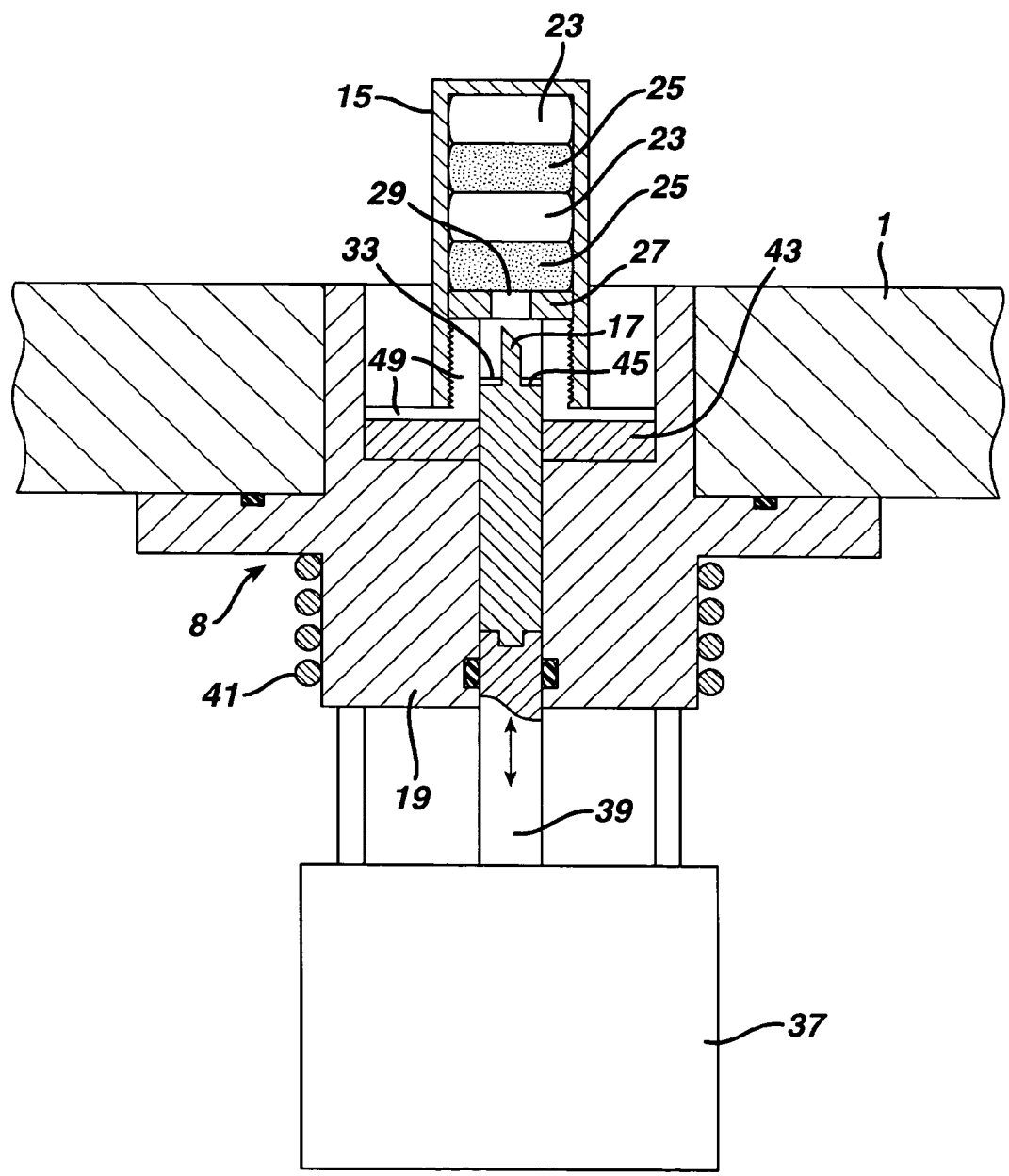
FIG. 5 is a sectional view of a sterilizing agent introducing device according to the embodiment 2 of the present invention.
Figure 6:
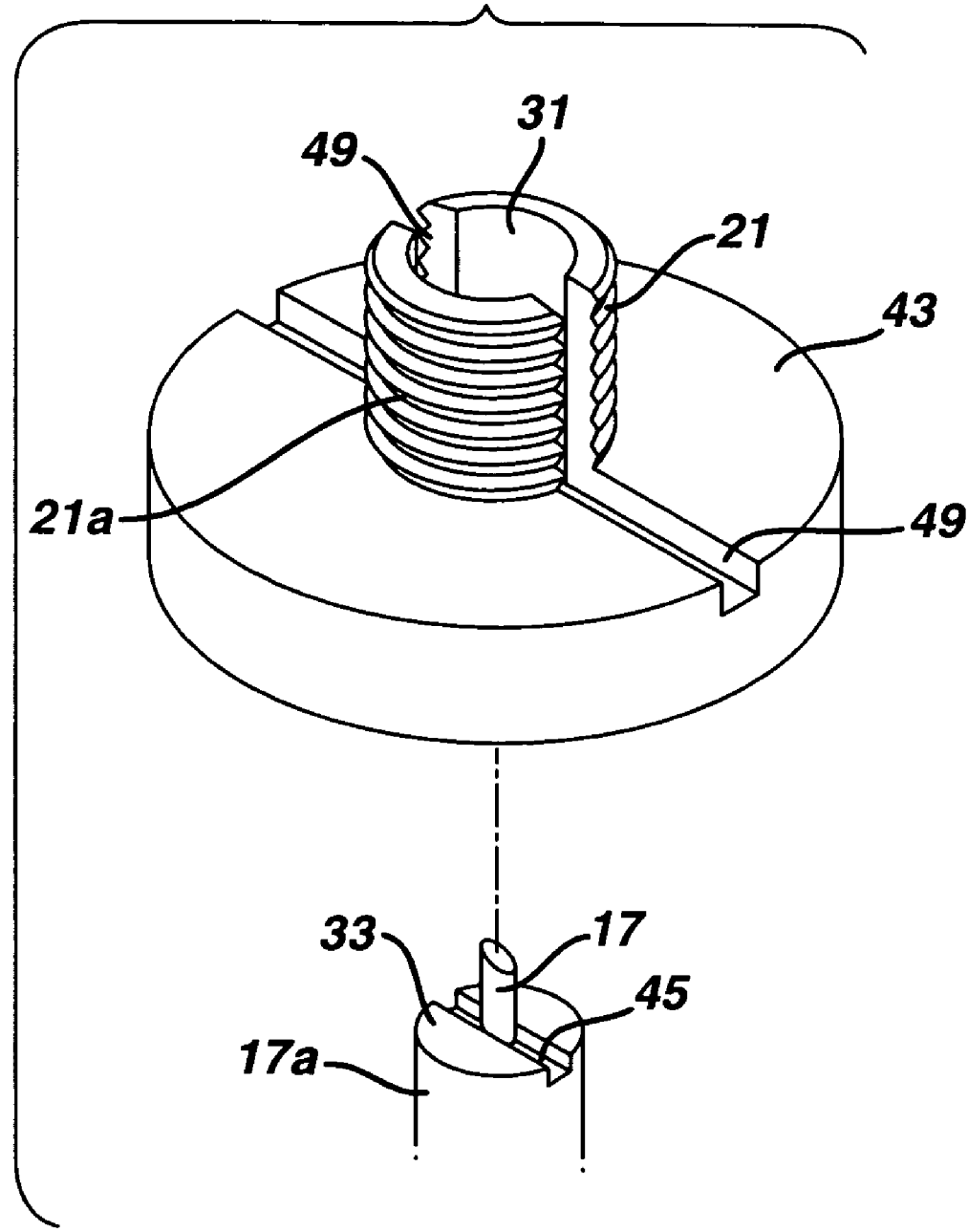
FIG. 6 is a disassembled perspective view of a needle and a mounting screw part of FIG. 5.

FIG. 5 is a sectional view showing a hydrogen peroxide introducing device of a sterilizer with a needle according to the embodiment 2 of the present invention and FIG. 6 is a disassembled perspective view of the needle and a mounting screw part 21 of FIG. 5. Like reference numerals denote like components of FIGS. 1 to 4 to omit overlapping explanation.

According to the embodiment 2, the needle 17 is formed to be cylindrical without a needle path. A guide groove 45 is formed in the pressing part 33 and a removal groove 49 opening upwardly is formed in the mounting screw part 21 and a base member 43 on which the mounting screw part 21 stands.

In the embodiment 2, when the needle 17 is lifted to puncture a sealed sterilizing agent capsule 25, a hydrogen peroxide solution in the sealed sterilizing agent capsule 25 is introduced to pass exteriorly of the needle 17 through the guide groove 43 and the removal groove 49 to the diffuser 19.

Thus, since the hydrogen peroxide solution does not pass in an interior such as a needle path, there is no clogging. A hydrogen peroxide solution can be stably taken out for a long period of time.

Embodiment 3

Figure 7:
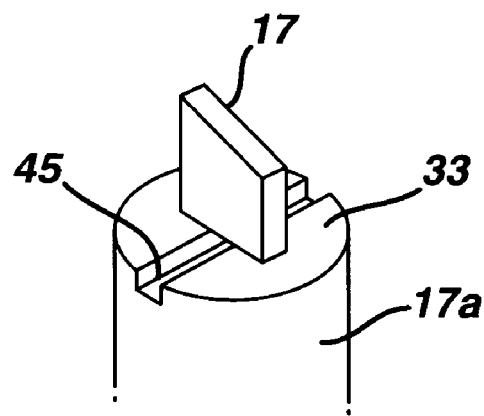
FIG. 7 is a perspective view of a needle according to the embodiment 3 of the present invention.

FIG. 7 is a perspective view of a needle according to the embodiment 3 of the present invention. Like reference numerals denote like components of FIG. 6 to omit overlapping explanation. A needle 17 according to the embodiment 3 is shaped to be a prism but similar in action and advantageous effect.

Embodiment 4

Figure 8:
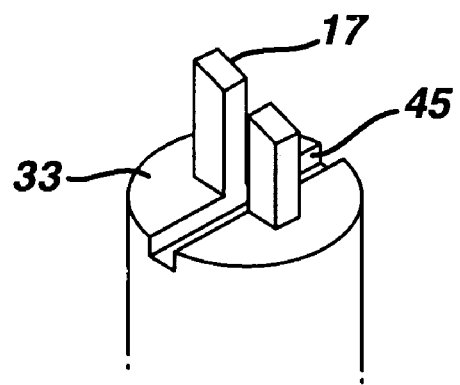
FIG. 8 is a perspective view of a needle according to the embodiment 4 of the present invention.

FIG. 8 is a perspective view of a needle according to the embodiment 4 of the present invention. Like reference numerals denote like components of FIGS. 6 and 7 to omit overlapping explanation. A needle 17 according to the embodiment 4 is shaped to be two prisms divided with a guide groove 45 but similar in action and advantageous effect.

Embodiment 5

Figure 9:
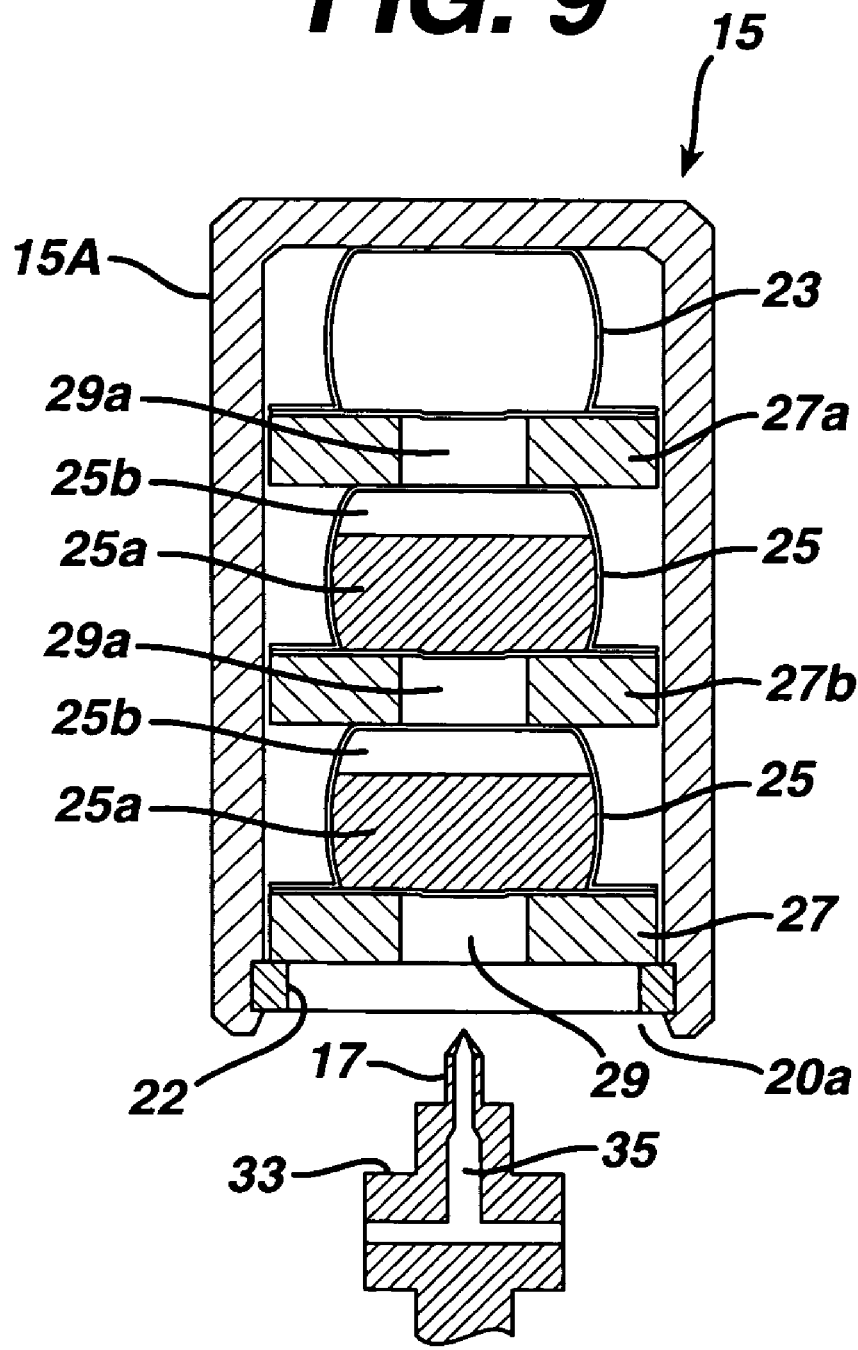
FIG. 9 is a sectional view of a capsule container of a sterilizer according to the embodiment 5 of the present invention.
Figure 10:
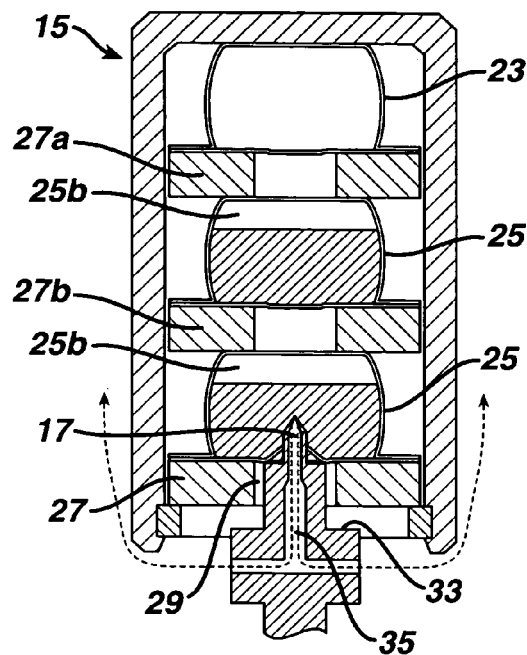
FIG. 10(a) to FIG. 10(e) are views for explaining the operation of the capsule container of FIG. 9.
Figure 10:
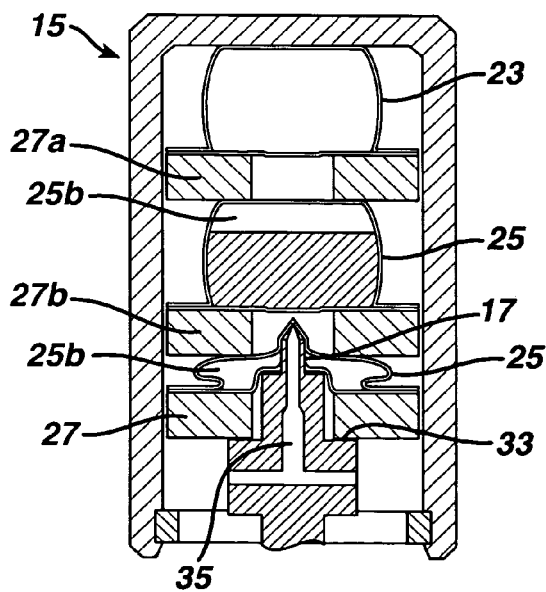
Figure 10:
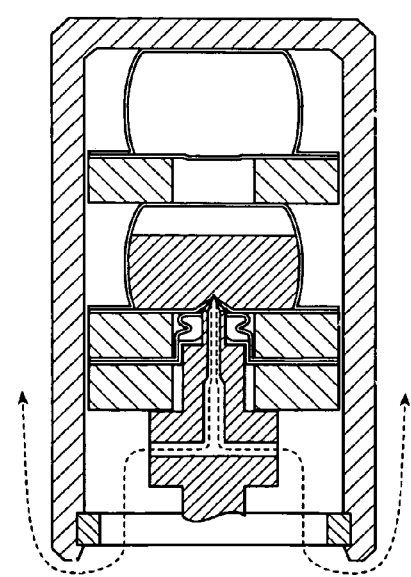
Figure 10:
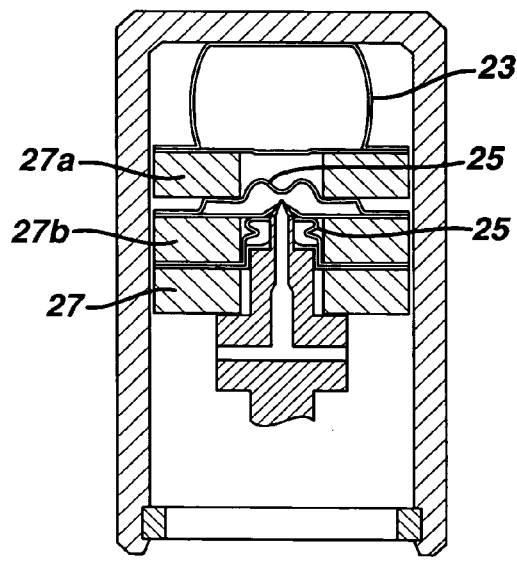
Figure 10:
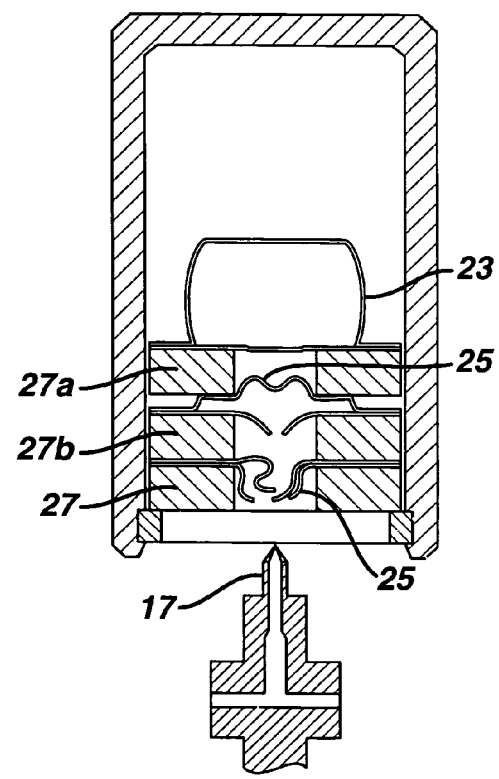

FIG. 9 is a sectional view of a sterilizing agent capsule container according to the embodiment 5 of the present invention. Like reference numerals denote like components of FIGS. 1 to 8.

In a sterilizing agent capsule container 15 according to the embodiment 5, inside a container body (capsule accommodation chamber) 15A with an open end 20a, a sealed gas capsule 23, a capsule support 27a for supporting the capsule 23, a sealed sterilizing agent capsule 25, a capsule support 27b for supporting the capsule 25, another sealed sterilizing agent capsule 25 and a capsule support 27 for supporting the capsule 25 are inserted from the open end 20a in sequence and they are accommodated in the axial direction of a needle 17.

A stopper member 22 such a C-ring is securely fitted in the open end 20a of the container body 15A to engage the capsule support 27 closest to the open end 20a with the stopper member 22. This engagement prevents the capsule support 27, and, further, the upper sealed sterilizing agent capsule 25, the capsule support 27b, the sealed sterilizing agent capsule 25, the capsule support 27a and the sealed gas capsule 23 from dropping out of the container body 15A.

The capsule supports 27a, 27b and 27 can move in the direction of compressing the sealed gas capsule 23 and the sealed sterilizing agent capsules 25 in the container body 15A which are disposed in the axial direction of the needle 17.

As mentioned above, the sealed gas capsule 23, the sealed sterilizing agent capsules 25 and the capsule supports 27a, 27b and 27 are alternately disposed in the container body 15A and the capsule support 27 closest to the open end 20a of the container body 15A is removably engaged with and supported against the stopper member 22.

A gas such as air is sealed in the gas capsule 23, while a liquid sterilizing agent 25a such a hydrogen peroxide solution and an aqueous peracetic acid solution (hereinafter referred to as a peracetic acid solution) is sealed in the sterilizing agent capsules 25 with a gas layer 25b therein. These capsules 23 and 25 are made of a material which the needle 17 can pass through.

Through holes 29a, 29b and 29 are provided in the centers of the capsule supports 27a, 27b and 27 which the needle 17 can pass through, and also function as a transpiration hole of a sterilizing agent when the needle 17 punctures the sealed sterilizing agent capsules 25.

The sterilizing agent capsule container 15 with the sealed gas capsule 23, the sealed sterilizing agent capsules 25 and the capsule supports 27a, 27b and 27 united in the container body 15A is assembled for use so that the open end 20a is in communication with a reduced-pressure housing of a sterilizer.

Next, its operation will be explained. FIGS. 10(a) to 10(e) are views for explaining the operation.

When either the sterilizing agent capsule container 15 or the needle 17 as shown in FIG. 9 is driven in the relative direction thereof, the needle 17 passes through the through hole 29 of the first capsule support 27 close to the open end 20a and punctures the first sealed sterilizing agent capsule 25 as shown in FIG. 10(a). A negative pressure exerted from the reduced-pressure housing of the sterilizer against a needle hole 35 of the needle puncturing the first sealed sterilizing agent capsule 25 causes a sterilizing agent inside the sealed sterilizing agent capsule 25 to diffuse (transpire) toward the inside of the reduced-pressure housing (beginning of first diffusion).

Next, as shown in FIG. 10(b), the pressing part 33 contacts and moves the first capsule support 27 to compress the first sealed sterilizing agent capsule 25. As a result, the first sealed sterilizing agent capsule 25 is compressed between the first capsule support 27 and the second capsule support 27b. The remainder of the sterilizing agent in the first sealed sterilizing agent capsule 25 diffuses together with a gas through the needle hole 35 to complete the first diffusion. In this case, the driving of the sterilizing agent capsule container 15 or the needle 17 is stopped at a position of the needle 17 shown in FIG. 10(b), that is, where the tip of the needle 17 is inserted into the through hole 29a of the second support capsule 27b but does not reach the second sealed sterilizing agent capsule 25.

When either the sterilizing agent capsule container 15 or the needle 17 is driven in the relative direction thereof again, the second diffusion begins as shown in FIG. 10(c). At the second diffusion beginning, the pressing part 33 of the needle 17 further moves the first capsule support 27 so that the first sealed sterilizing agent capsule 25 is completely compressed between the first and second capsule supports 27 and 27b, and at the same time the needle 17 passes through the first sealed sterilizing agent capsule 25 to puncture the second sealed sterilizing agent capsule 25. As a result, like the first diffusion, a sterilizing agent inside the second sealed sterilizing agent capsule 25 diffuses in the form of a mist through the needle hole 35 of the needle 17. Next, the first capsule support 27, which engages the pressing part 33 of the needle 17 and moves integrally with the needle 17, presses and moves the second capsule support 27b with the first sealed sterilizing agent capsule 25 compressed therebetween. Consequently, the second sealed sterilizing agent capsule 25 is compressed between the second capsule support 27b and the third capsule support 27a so that all the amount of a sterilizing agent in the second sealed sterilizing agent capsule 25 can securely diffuse. The driving of the sterilizing agent capsule container 15 or the needle 17 is stopped to complete the second diffusion in the sate shown in FIG. 10(d). In this state, the needle 17 remains at a position where it punctures but does not pass through the second sealed sterilizing agent capsule 25.

After the completion of the second diffusion, as shown in FIG. 10(e), the sterilizing agent capsule container 15 or the needle 17 is driven to move rearwardly in the direction of removing the needle 17 from the sterilizing agent capsule container 15. The use of the sterilizing agent capsule container 15 then ends.

In the embodiment 5, the number of the sealed sterilizing agent capsules 25 accommodated in the sterilizing agent capsule container 15 is plural, not limited to two.

According to the embodiment 5 stated above, the sterilizing agent capsule container 15 is constructed such that the sealed gas capsule 23 and a plurality of the sealed sterilizing agent capsules 25 following the sealed gas capsule 23 are accommodated in the container body 15A and the needle 17 can pass through these capsules. Thus, a large moving device for horizontally moving a sterilizing agent capsule container 15 and displacing individual sealed sterilizing agent capsules 25 to a certain removal position corresponding to a needle, and a pressurizing device for pressurizing and compressing a sealed sterilizing agent capsule 25 at the removal position are not required in a sterilizer with the sterilizing agent capsule container 15 mounted therein. As a result, the space occupied by the capsule container 15 can be reduced and the construction thereof can be simplified, thereby decreasing the cost.

Further, as stated above, the sealed gas capsule 23 and a plurality of the sealed sterilizing agent capsules 25 accommodated in the sterilizing agent capsule container 15 are individually supported by the capsule supports 27a, 27a and 27 which can move therein and through which the needle 17 can pass. Thus, the sealed gas capsule 23 and the sealed sterilizing agent capsules 25 can be stably supported in the direction of compression and a plurality of the sealed sterilizing agent capsules 25 can be gradually smoothly broken by the needle 17. In addition, since a gas layer 25b is formed in each sealed sterilizing agent capsule 25 and the sealed gas capsule 23 is disposed at the deepest position of the container body 15A, the sealed sterilizing agent capsules 25 and the capsule supports 27a, 27b and 27 can be more stably supported in the direction of compression with a cushion effect. The sealed sterilizing agent capsules 25 can be also protected against breakage.

Further, according to the embodiment 5, even if the pressure inside the sterilizing agent capsule container 15 is normal, the sealed gas capsule 23, the sealed sterilizing agent capsules 25 and the capsule supports 27a, 27b and 27 can be maintained in the sterilizing agent capsule container 15 in proper compression by the sealed gas capsule 23 and the gas layers 25b in the sealed sterilizing agent capsules 25. Thus, even under a normal pressure, the sealed gas capsule 23, the sealed sterilizing agent capsules 25 and the capsule supports 27a, 27b and 27 can be more stably supported in the sterilizing agent capsule container 15, and, further, under a reduced-pressure, since the sealed gas capsule 23 and the sealed sterilizing agent capsules 25 are compressed and deformed, the stability can be maintained, allowing smooth actions.

Embodiment 6

Figure 11:
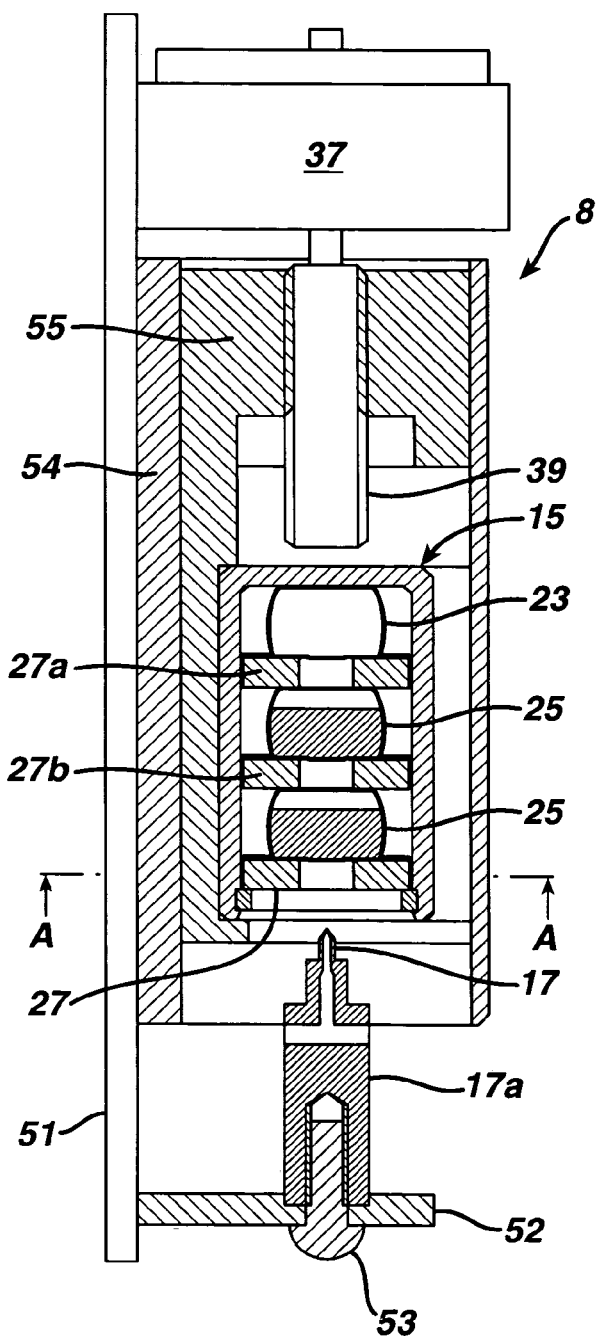
FIG. 11 is a sectional view of a sterilizer according to the embodiment 6 of the present invention.
Figure 12:
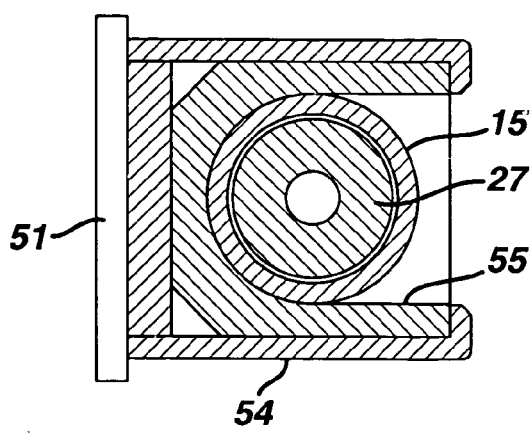
FIG. 12 is a sectional view along the line A—A of FIG. 11.
Figure 13:
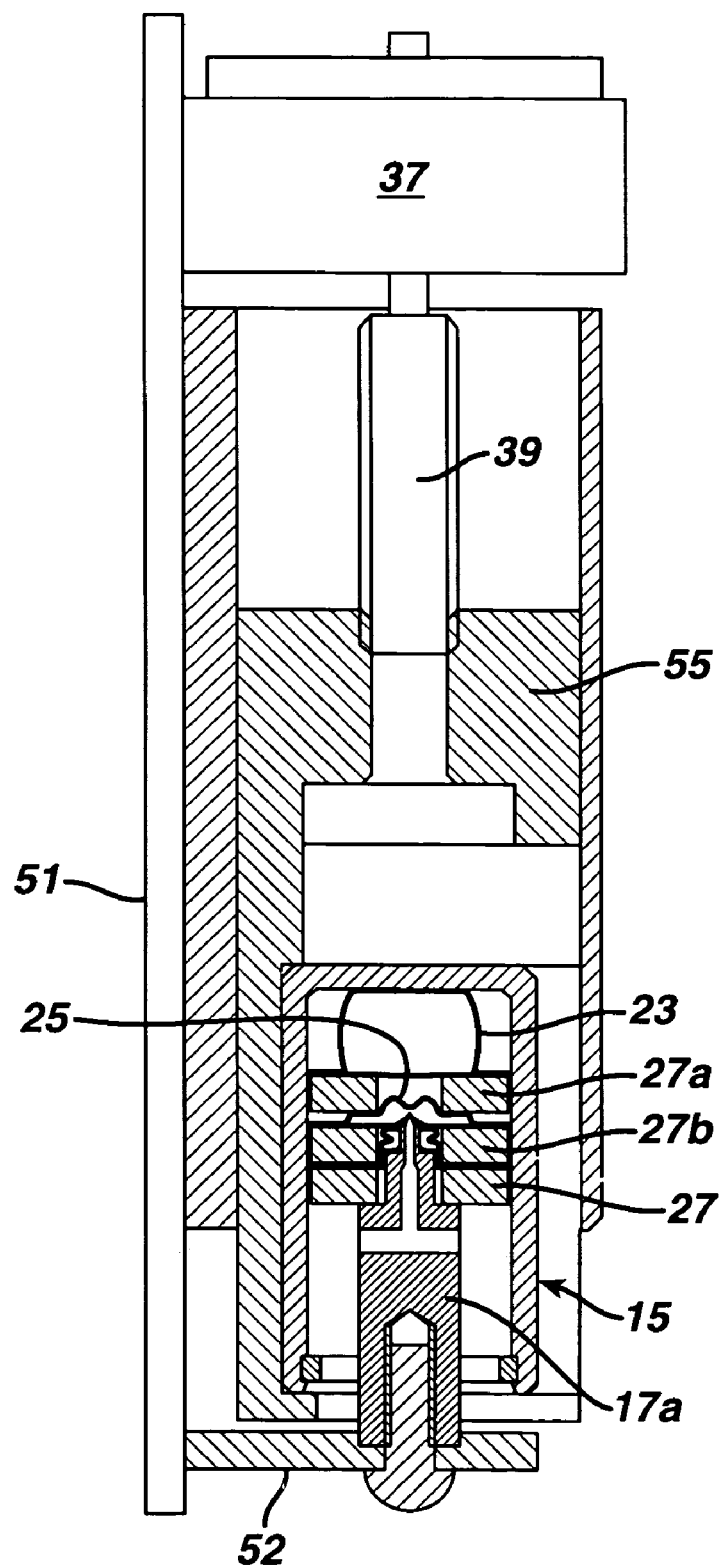
FIG. 13 is a view for explaining the operation of the sterilizer of FIG. 11.

FIG. 11 is a sectional view of a sterilizer according to the embodiment 6 of the present invention, FIG. 12 is a sectional view along the line A—A of FIG. 11 and FIG. 13 is a view for explaining an operation of the sterilizer shown in FIG. 11. Like reference numerals denote like components of FIGS. 1 to 10 to omit overlapping explanation.

In these figures, the reference numeral 51 denotes a chassis of a hydrogen peroxide introducing device 8 to be mounted in a sterilizer. The reference numeral 52 is an arm projected from and integrated with an end of the chassis 51. A needle 17 is securely fixed to the arm 52 with a screw 53. A driving member (stepping motor) 37 is held in the other end of the chassis 51.

The reference numeral 54 denotes a frame fixed to and integrated with the chassis 51. The transverse section of the frame 54 is shown in FIG. 12.

The reference numeral 55 denotes a container holder mounted in the frame 54, which holder can move between the needle 17 and the driving member 37 in the axial direction of the needle 17. The container holder 55 has a container setting part 55a with a U-like section in which a sterilizing agent capsule container 15 can be removably mounted.

An output rotational axis (screw rod) 39 of the driving member 37 is screwed through the container holder 55. When the driving member 37 drives the rotational rod 39 to rotate in opposite directions, thereby allowing the reciprocation of the container holder 55.

Next, an operation of the sterilizer will be explained.

When the driving member 37 is activated so that the output rotational axis 39 rotates in one direction, the container holder 55 is screwed and moves toward the needle 17. As a result, a plurality of sealed sterilizing agent capsules 25 in the capsule container 15 held in the container holder 55 are gradually punctured in sequence in the same manner as the embodiment 5. A sterilizing agent in the sealed sterilizing agent capsules 25 punctured by the needle 17 can diffuse in a reduced-pressure housing of a sterilizer in the same manner as the embodiments 1 and 5. After a sterilizing agent in all the sealed sterilizing agent capsules 25 in the sterilizing agent capsule container 15 has diffused by punctures of the needle, when the driving member 37 is activated in the reverse direction, the sterilizing agent capsule container 15 can move integrally with the container holder 55 in the direction apart from the needle 17. At a stop position of the container holder 55, the sterilizing agent capsule container 15 can be replaced.

In the embodiment 1, the needle 17 punctures a sealed sterilizing agent capsule 25 by diving the needle 17 while fixing the sterilizing agent capsule container 15, but, on the other hand, in the embodiment 6, the needle 17 punctures a sealed sterilizing agent capsule 25 by driving the sterilizing agent capsule container 15 while fixing the needle 17.

In the embodiment 6, the sterilizing agent capsule container 15 can be moved close to or apart from the fixed needle 17 together with the container holder 55 by the driving member 37 to obtain the same advantageous effects as those of the embodiments 1 to 5.

In the sterilizing agent capsule containers 15 of all the embodiments, a sterilizing agent inside a sealed sterilizing agent capsule 25 accommodated in the container body 15A may be any sterilizing agent which can be vaporized to a chemical vapor by contact with a gas (air) at the time of puncture by the needle 17. The diffuser becomes unnecessary by the use of such a sterilizing agent.

The following embodiments are also contained in the present invention.

(1) A capsule container of a low-temperature plasma sterilizer having a container body with an insert open end to be set in a vacuum housing of the low-temperature plasma sterilizer, sealed hydrogen peroxide capsules containing a hydrogen peroxide solution and sealed air capsules containing air being inserted from the open end into the container body to be alternately stacked in the container body, the lowest capsule being supported by a capsule support with an insert hole through which a needle passes, the capsule support capable of moving vertically.

(2) The capsule container of the embodiment (1), wherein the hydrogen peroxide capsules and the air capsules are made of a material which the needle inserted from the insert hole can puncture to pass through.

(3) The capsule container of the embodiment (1) or (2), wherein as the needle is lifted, the needle raises the capsule support together with the needle.

(4) A low-temperature plasma sterilizer comprising:
an evaporator for gasifying a hydrogen peroxide solution, communicating with a vacuum housing which serves as a sterilizing chamber;
a capsule container disposed in the vacuum housing, where sealed hydrogen peroxide capsules containing a hydrogen peroxide solution and sealed air capsules containing air are alternately stacked, the air capsules capable of expanding corresponding to a vacuum degree of the vacuum housing; and
a needle capable of being lifted into the capsule container by a driving part to puncture a hydrogen peroxide capsule so as to introduce a hydrogen peroxide solution therefrom to the evaporator;
wherein every time the needle is lifted in a step, the needle punctures the lowest hydrogen peroxide capsule in sequence.

(5) The low-temperature plasma sterilizer of the embodiment (4), wherein a hydrogen peroxide solution in a hydrogen peroxide capsule punctured by the needle is introduced to pass exteriorly of the needle to the evaporator.

(6) The low-temperature plasma sterilizer of the embodiment (4), wherein the needle has a raising part for raising a deflated hydrogen peroxide capsule upwardly after completely taking out a hydrogen peroxide solution.

INDUSTRIAL UTILITY

As mentioned above, according to the sterilizer of the present invention, since a sealed sterilizing agent capsule accommodated in a capsule accommodation container is pressurized by a forcing member accommodated in the capsule accommodation container, a sterilizing agent in the sealed sterilizing agent capsule can be easily introduced into an evaporator only by activating a needle to puncture it.

The invention claimed is:

1. A sterilizing agent capsule container in communication with a reduced-pressure housing of a sterilizer,
the sterilizing agent capsule container comprising:
a capsule accommodation chamber, and
a plurality of sealed sterilizing agent capsules accommodated in the capsule accommodation chamber in an axial direction of a needle for removing a sterilizing agent, the sealed sterilizing agent capsules made of a material which the needle can pass through; and
wherein a plurality of capsules are accommodated in the capsule accommodation chamber and at least two of the capsules are sealed sterilizing agent capsules.

2. The sterilizing agent capsule container according to claim 1 wherein a plurality of sealed sterilizing agent capsules and a plurality of sealed gas capsules are alternately accommodated in the capsule accommodation chamber.

3. The sterilizing agent capsule container according to claim 1 wherein a plurality of sealed sterilizing agent capsules and a capsule support which the needle can pass through are accommodated in the capsule accommodation chamber.

4. The sterilizing agent capsule container according to claim 1 wherein a plurality of sealed sterilizing agent capsules and a plurality of capsule supports are alternately accommodated in the capsule accommodation chamber.

5. The sterilizing agent capsule container according to claim 1 wherein a plurality of sealed sterilizing agent capsules, a sealed gas capsule and a capsule support which the needle can pass through are combined and accommodated in the capsule accommodation chamber.

6. The sterilizing agent capsule container according to claim 5 wherein the sealed sterilizing agent capsules and sealed gas capsules or capsule supports are alternately disposed in the capsule accommodation chamber and a sealed sterilizing agent capsule closest to an insert opening of the capsule accommodation chamber is supported by a capsule support movably disposed in the capsule accommodation chamber.

7. The sterilizing agent capsule container according to claim 1 wherein the sterilizing agent in the sealed sterilizing agent capsules is a hydrogen peroxide solution or a peracetic acid solution.

8. The sterilizing agent capsule container according to claim 1 wherein the sealed sterilizing agent capsules contain a gas layer therein.

9. A sterilizer comprising:
a sterilizing agent capsule container in communication with a reduced-pressure housing serving as a sterilization chamber;
a plurality of sealed sterilizing agent capsules with a sterilizing agent sealed therein to be mounted in a capsule accommodation chamber of the sterilizing agent capsule container;
a needle capable of passing through the sealed sterilizing agent capsules to take the sterilizing agent therefrom; and
a driving member for driving the needle or the sterilizing agent capsule container so that the needle can puncture the sealed sterilizing agent capsules in the sterilizing agent capsule container in an axial direction of the needle in sequence.

10. The sterilizer according to claim 9 wherein the needle has a pressing part for pressing a sealed sterilizing agent capsule in a direction of compression.

11. The sterilizer according to claim 9 wherein the sterilizing agent capsule container communicates with the reduced-pressure housing through a diffuser whereby when the needle punctures a sealed sterilizing agent capsule, the diffuser introduces a sterilizing agent transpired from the sealed sterilizing agent capsule.

12. The sterilizer according to claim 9 further comprising means for generating a low-temperature plasma is generated in the reduced-pressure housing.

13. The sterilizer according to claim 9 wherein the sterilizing agent in the sealed sterilizing agent capsules is a hydrogen peroxide solution or a peracetic acid solution.

* * * * *